(12) United States Patent
Morgan et al.

(10) Patent No.: US 11,547,445 B2
(45) Date of Patent: Jan. 10, 2023

(54) POWERED DRIVER ACTUATED BY FORCE ON DRIVESHAFT AND RELATED KITS, COMPONENTS, AND METHODS

(71) Applicant: TELEFLEX LIFE SCIENCES LIMITED, Valletta (MT)

(72) Inventors: John Morgan, Shavano Park, TX (US); Larry J. Miller, Shavano Park, TX (US); Robert W. Titkemeyer, Shavano Park, TX (US); Chris Kilcoin, Shavano Park, TX (US)

(73) Assignee: TELEFLEX LIFE SCIENCES LIMITED, Valletta (MT)

( * ) Notice: Subject to any disclaimer, the term of this patent is extended or adjusted under 35 U.S.C. 154(b) by 421 days.

(21) Appl. No.: 16/875,338

(22) Filed: May 15, 2020

(65) Prior Publication Data
US 2020/0275952 A1 Sep. 3, 2020

Related U.S. Application Data

(63) Continuation of application No. 16/135,161, filed on Sep. 19, 2018, now Pat. No. 10,653,448, which is a
(Continued)

(51) Int. Cl.
*A61B 17/00* (2006.01)
*A61B 17/34* (2006.01)
(Continued)

(52) U.S. Cl.
CPC ........ *A61B 17/3476* (2013.01); *A61B 10/025* (2013.01); *A61B 17/3472* (2013.01);
(Continued)

(58) Field of Classification Search
CPC combination set(s) only.
See application file for complete search history.

(56) References Cited

U.S. PATENT DOCUMENTS

| 1,954,620 A | 4/1934 | Connel |
| 5,709,275 A | 1/1998 | Neumaier |

(Continued)

FOREIGN PATENT DOCUMENTS

| CN | 1117838 A | 3/1996 |
| CN | 1418760 A | 5/2003 |

(Continued)

OTHER PUBLICATIONS

Decision to Grant a Patent issued in Japanese Application No. 2016-552558 dated Jan. 25, 2021 [with English translation].

*Primary Examiner* — Sameh R Boles
(74) *Attorney, Agent, or Firm* — BakerHostetler

(57) ABSTRACT

Powered drivers operable to insert an intraosseous device into a bone are disclosed. Some of the present powered drivers include a housing having a distal end and a proximal end. A driveshaft may be located near the distal end of the housing and configured to engage a portion of the intraosseous device. A motor may be disposed in the housing and operable to rotate the driveshaft. A power source may be disposed within the housing and configured to power the motor. The powered drivers may include a lockout operable to prevent activation of the driver for increased safety when handling the driver.

20 Claims, 13 Drawing Sheets

Related U.S. Application Data continuation of application No. 14/624,219, filed on Feb. 17, 2015, now Pat. No. 10,092,320.

(60) Provisional application No. 61/945,325, filed on Feb. 27, 2014, provisional application No. 61/940,741, filed on Feb. 17, 2014.

(51) Int. Cl.
    *A61B 10/02*     (2006.01)
    *A61B 17/16*     (2006.01)

(52) U.S. Cl.
    CPC ....... *A61B 17/1622* (2013.01); *A61B 17/1637* (2013.01); *A61B 2010/0258* (2013.01); *A61B 2017/00398* (2013.01); *A61B 2017/00734* (2013.01)

(56) References Cited

U.S. PATENT DOCUMENTS

| | | | |
|---|---|---|---|
| 5,747,953 | A | 5/1998 | Philipp |
| 7,914,461 | B2 | 3/2011 | Richard et al. |
| 11,103,281 | B2 | 8/2021 | Miller |
| 2003/0225411 | A1 | 12/2003 | Miller |
| 2005/0082389 | A1 | 4/2005 | Sanchez et al. |
| 2005/0131345 | A1 | 6/2005 | Miller |
| 2005/0165404 | A1 | 7/2005 | Miller |
| 2005/0221580 | A1 | 10/2005 | Saitou et al. |
| 2008/0215056 | A1 | 9/2008 | Miller et al. |
| 2008/0221580 | A1 | 9/2008 | Miller et al. |
| 2009/0093830 | A1 | 4/2009 | Miller |
| 2011/0054484 | A1 | 3/2011 | Brandon |
| 2011/0203821 | A1* | 8/2011 | Puzio .................. B25B 23/0064 173/176 |
| 2012/0112687 | A1 | 5/2012 | Houser et al. |
| 2015/0171504 | A1 | 6/2015 | Hotta |

FOREIGN PATENT DOCUMENTS

| | | |
|---|---|---|
| CN | 1909846 A | 2/2007 |
| CN | 101133972 A | 3/2008 |
| CN | 101365390 A | 2/2009 |
| CN | 101401736 A | 4/2009 |
| CN | 101536926 A | 9/2009 |
| CN | 101687067 A | 3/2010 |
| CN | 102131469 A | 7/2011 |
| CN | 102670265 A | 9/2012 |
| CN | 102753782 A | 10/2012 |
| CN | 103558786 A | 2/2014 |
| JP | 37-20988 Y | 8/1962 |
| JP | 2008062341 A | 3/2008 |
| JP | 2008541784 A | 11/2008 |
| JP | 2013516335 A | 5/2013 |
| JP | 2013545538 A | 12/2013 |
| TW | 201247187 A | 12/2012 |
| WO | 2011085194 A1 | 7/2011 |
| WO | 2012175946 A1 | 12/2012 |
| WO | 2013171585 A2 | 11/2013 |

\* cited by examiner

POWERED DRIVER ACTUATED BY FORCE ON DRIVESHAFT AND RELATED KITS, COMPONENTS, AND METHODS

CROSS-REFERENCED TO RELATED APPLICATION

This application is a continuation application of U.S. patent application Ser. No. 16/135,161 filed Sep. 19, 2018, which is a continuation application of U.S. patent application Ser. No. 14/624,219 filed Feb. 17, 2015, now U.S. Pat. No. 10,092,320, which claims priority to U.S. Provisional Patent Application No. 61/940,741 filed Feb. 17, 2014 and U.S. Provisional Patent Application No. 61/945,325 filed Feb. 27, 2014, the entire contents of which are incorporated herein by reference.

FIELD OF INVENTION

The present invention is generally related to powered drivers and more particularly, but not by way of limitation, to powered drivers actuated by a force on a driveshaft (e.g., for inserting an intraosseous device into a patient's bone).

BACKGROUND

Examples of powered drivers for inserting an intraosseous device are disclosed in U.S. patent application Ser. No. 12/025,580, which is published as Pub. No. US 2008/0221580.

SUMMARY

Embodiments of the present drivers and kits can be configured to assist a user with inserting an intraosseous (TO) device into a patient's bone.

Some embodiments of the present apparatuses or drivers comprise: a housing having a distal end and a proximal end; a motor disposed in the housing; a driveshaft extending outward from the distal end of the housing in a direction away from the proximal end; a gearbox coupled to the motor and to the driveshaft such that activation of the motor will cause rotation of the driveshaft; and a battery configured to power the motor; where the gearbox is slidably disposed in the housing and configured such that, upon application of a threshold force on the driveshaft in the direction of the proximal end of the housing, the driveshaft and gearbox will slide toward the proximal end of the housing and thereby close an electrical circuit between the motor and the battery. In some embodiments, the driveshaft is biased in the direction of the distal end of the housing (e.g., by a spring disposed between the gearbox and the distal end of the housing).

Some embodiments of the present drivers further comprise: a switch coupled to the battery and the motor, the switch disposed between the proximal end of the housing and at least a portion of the gearbox; where the switch is configured to close the circuit upon application of the threshold force on the driveshaft. In some embodiments, the switch is disposed between the motor and the proximal end of the housing. In some embodiments, the switch comprises a base and plunger axially movable relative to the base. In some embodiments, the motor and gearbox are coupled in fixed axial relation to each other and are together slidable within the housing. In some embodiments, the motor and gearbox are biased in the direction of the distal end of the housing (e.g., by a spring disposed between the motor and the distal end of the housing).

In some embodiments of the present drivers, the housing defines a primary portion extending between the distal end and the proximal end, and a handle portion extending laterally from the primary portion at a non-parallel angle relative to a longitudinal axis of the primary portion. In some embodiments, at least a portion of the driveshaft has an equilateral polygonal cross-sectional shape. In some embodiments, the at least a portion of the driveshaft has a pentagonal cross-sectional shape.

Some embodiments of the present drivers further comprise: an electrical lockout comprising a strip configured to be removably inserted into the housing between two electrically conductive portions of the electrical circuit to prevent the apparatus from energizing during sterilization. In some embodiments, the strip comprises a polymer (e.g., Mylar).

Some embodiments of the present drivers further comprise: a mechanical lockout including a tab configured to be removably inserted into the housing proximal to at least a portion of the driveshaft such that upon application of the threshold force on the driveshaft in the direction of the proximal end of the housing, the mechanical lockout prevents the driveshaft and gearbox from sliding toward the proximal end of the housing and thereby prevents the driveshaft and gearbox from closing the electrical circuit between the motor and the battery. In some embodiments, the mechanical lockout includes a needle cover. Some embodiments further comprise: an electrical lockout comprising a strip configured to be removably inserted into the housing between two electrically conductive portions of the electrical circuit to prevent the apparatus from energizing during sterilization; where the mechanical lockout is coupled to the electrical lockout.

Some embodiments of the present kits comprise: an embodiment of the present apparatuses; and an intraosseous device comprising a connector configured to be coupled to the driveshaft of the driver. In some embodiments, the connector comprises a recess configured to receive a distal end of the driveshaft. In some embodiments, the intraosseous device comprises: a hub; a cannula extending from the hub to a distal end spaced from the hub; and a trocar extending from the connector to a distal end spaced from the connector; where the cannula is configured to be inserted into the cannula and the connector coupled to the hub to hold the trocar in fixed relation to the cannula. In some embodiments, connector is configured to be coupled to the hub by a Luer lock connector. In some embodiments, the connector comprises a female threaded portion surrounding a portion of the trocar, the hub comprises a male threaded portion extending away from the distal end of the cannula, and the male threaded portion is configured to be coupled to the female threaded portion to couple the connector to the hub.

Some embodiments of the present methods comprise: disposing a distal end of an intraosseous (IO) device at a desired insertion site on a patient, the IO device coupled to the driveshaft of an embodiment of the present apparatuses; and applying a force to the distal end of the IO device via the housing of the driver such that the driveshaft of the driver slides toward the proximal end of the housing relative to the housing and activates the motor of the driver to rotate the driveshaft and IO device. In some embodiments, the force is applied until the IO device is inserted into a bone of the patient. In some embodiments, the desired insertion site is disposed over a proximal portion of the patient's humerus, a proximal portion of the patient's tibia, a distal portion of the patient's femur, a patient's clavicle, a patients iliac crest, or a patient's calcaneous. In some embodiments, the desired insertion site is disposed over the patient's sternum.

Some embodiments of the present apparatuses or drivers comprise: a housing having a distal end and a proximal end; a motor disposed in the housing; a driveshaft extending outward from the distal end of the housing in a direction away from the proximal end; a gearbox coupled to the motor and to the driveshaft such that activation of the motor will cause rotation of the driveshaft; a battery configured to power the motor; and a mechanical lockout including a tab configured to be removably inserted into the housing proximal to at least a portion of the driveshaft such that upon application of a threshold force on the driveshaft in the direction of the proximal end of the housing, the mechanical lockout prevents the driveshaft and gearbox from closing an electrical circuit between the motor and the battery. In some embodiments, the mechanical lockout includes a needle cover:

Some embodiments of the present apparatuses or drivers comprise: a housing having a distal end and a proximal end; a motor disposed in the housing; a driveshaft extending outward from the distal end of the housing in a direction away from the proximal end; a gearbox coupled to the motor and to the driveshaft such that activation of the motor will cause rotation of the driveshaft; a battery configured to power the motor; an electrical lockout comprising a strip configured to be removably inserted into the housing between two electrically conductive portions of an electrical circuit to prevent the apparatus from energizing during sterilization.

The term "coupled" is defined as connected, although not necessarily directly, and not necessarily mechanically; two items that are "coupled" may be unitary with each other. The terms "a" and "an" are defined as one or more unless this disclosure explicitly requires otherwise. The term "substantially" is defined as largely but not necessarily wholly what is specified (and includes what is specified; e.g., substantially 90 degrees includes 90 degrees and substantially parallel includes parallel), as understood by a person of ordinary skill in the art. In any disclosed embodiment, the terms "substantially," "approximately," and "about" may be substituted with "within [a percentage] of" what is specified, where the percentage includes 0.1, 1, 5, and 10 percent.

Further, a device or system that is configured in a certain way is configured in at least that way, but it can also be configured in other ways than those specifically described.

The terms "comprise" (and any form of comprise, such as "comprises" and "comprising"), "have" (and any form of have, such as "has" and "having"), "include" (and any form of include, such as "includes" and "including"), and "contain" (and any form of contain, such as "contains" and "containing") are open-ended linking verbs. As a result, an apparatus that "comprises," "has," "includes," or "contains" one or more elements possesses those one or more elements, but is not limited to possessing only those elements. Likewise, a method that "comprises," "has," "includes," or "contains" one or more steps possesses those one or more steps, but is not limited to possessing only those one or more steps.

Any embodiment of any of the apparatuses, systems, and methods can consist of or consist essentially of—rather than comprise/include/contain/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

The feature or features of one embodiment may be applied to other embodiments, even though not described or illustrated, unless expressly prohibited by this disclosure or the nature of the embodiments.

Some details associated with the embodiments described above and others are described below.

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers. The embodiments of the present assistive devices, coupler assemblies, drivers, intraosseous (IO) devices, and their components shown in the figures are drawn to scale for at least the embodiments shown.

DETAILED DESCRIPTION OF ILLUSTRATIVE EMBODIMENTS

Figure 1:
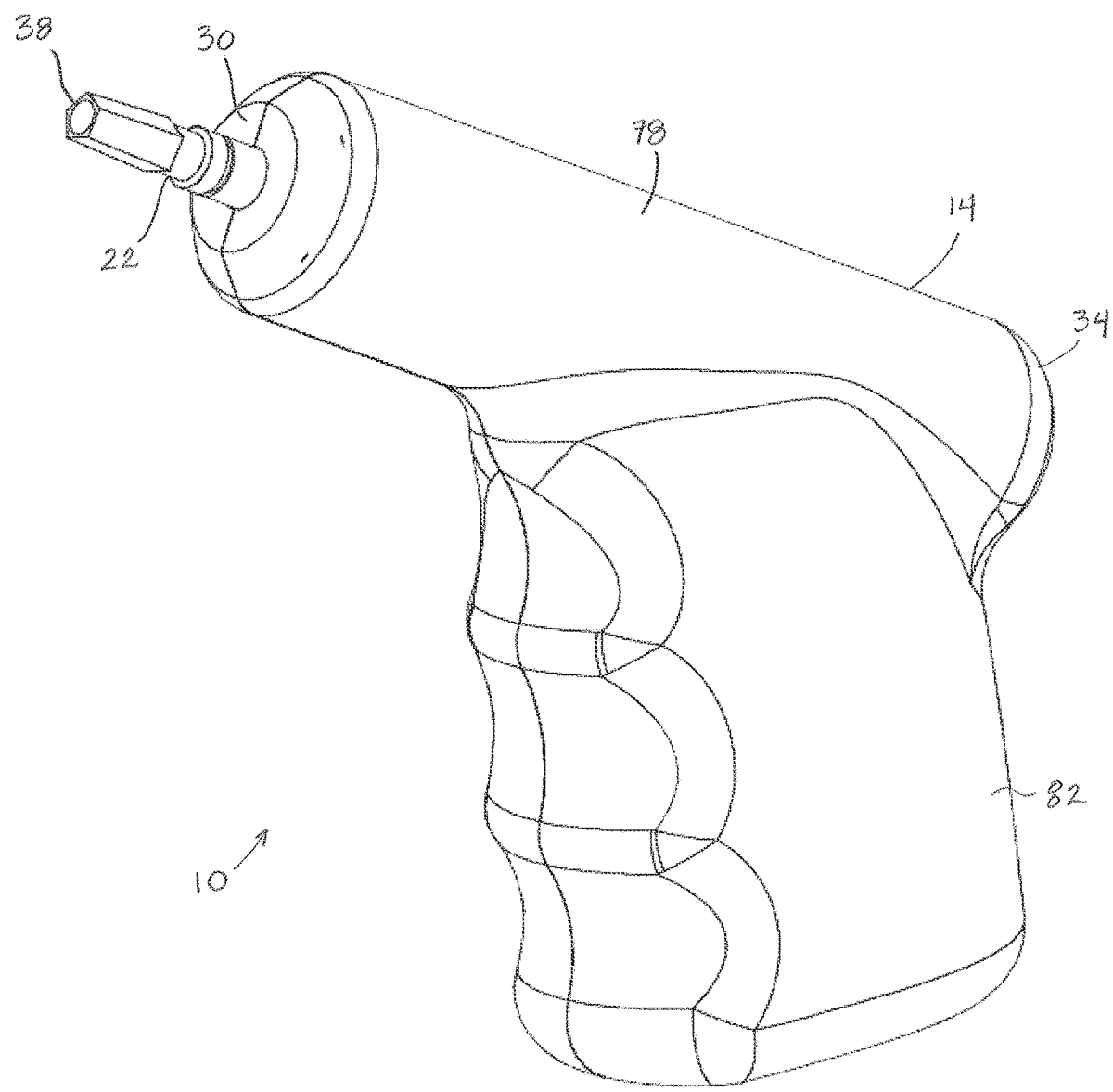
FIGS. 1 and 2 depict perspective views of a first embodiment of the present drivers.
Figure 2:
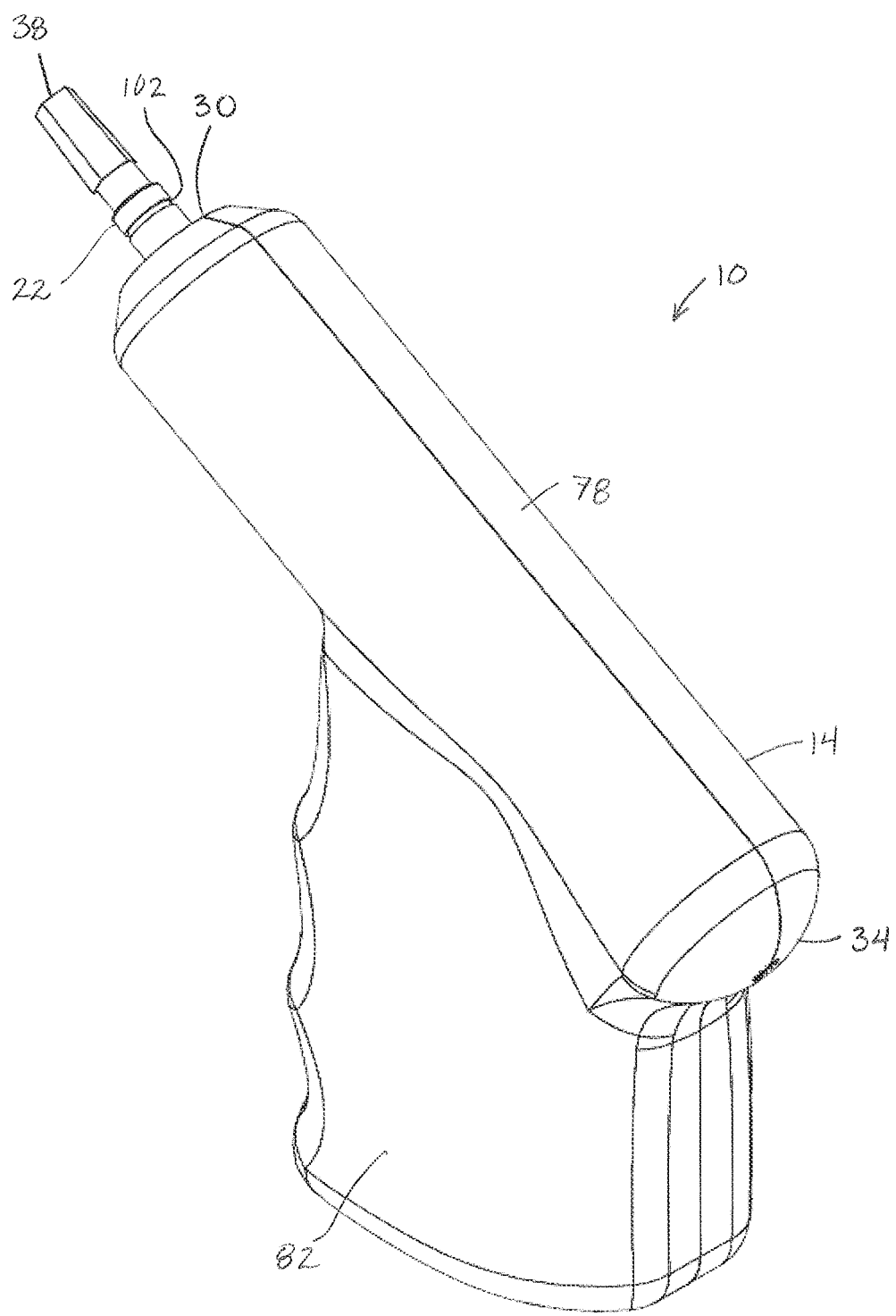
Figure 3A:
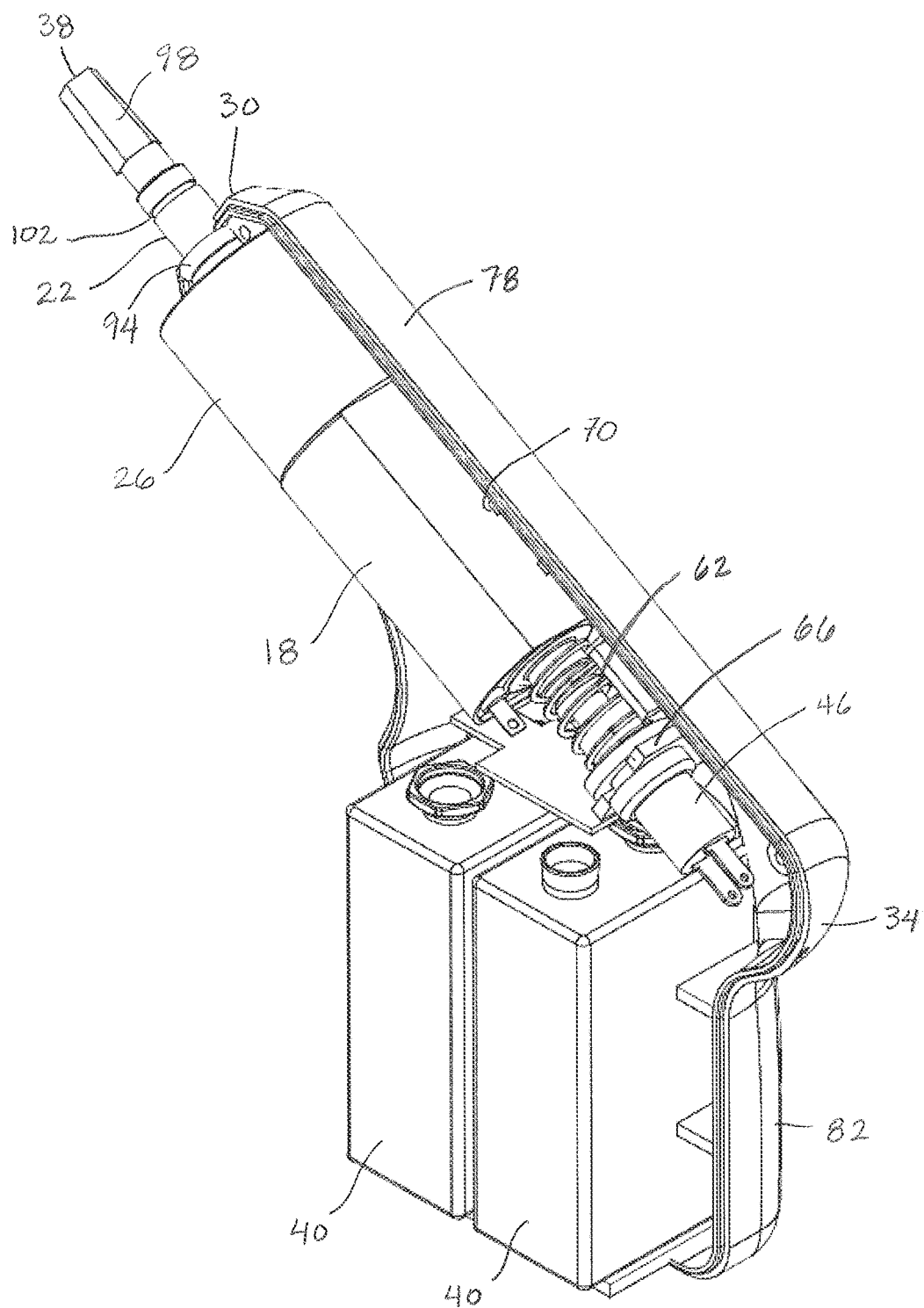
FIGS. 3A and 3B depict a cutaway perspective view and a side view, respectively, of the driver of FIGS. 1-2.
Figure 3B:
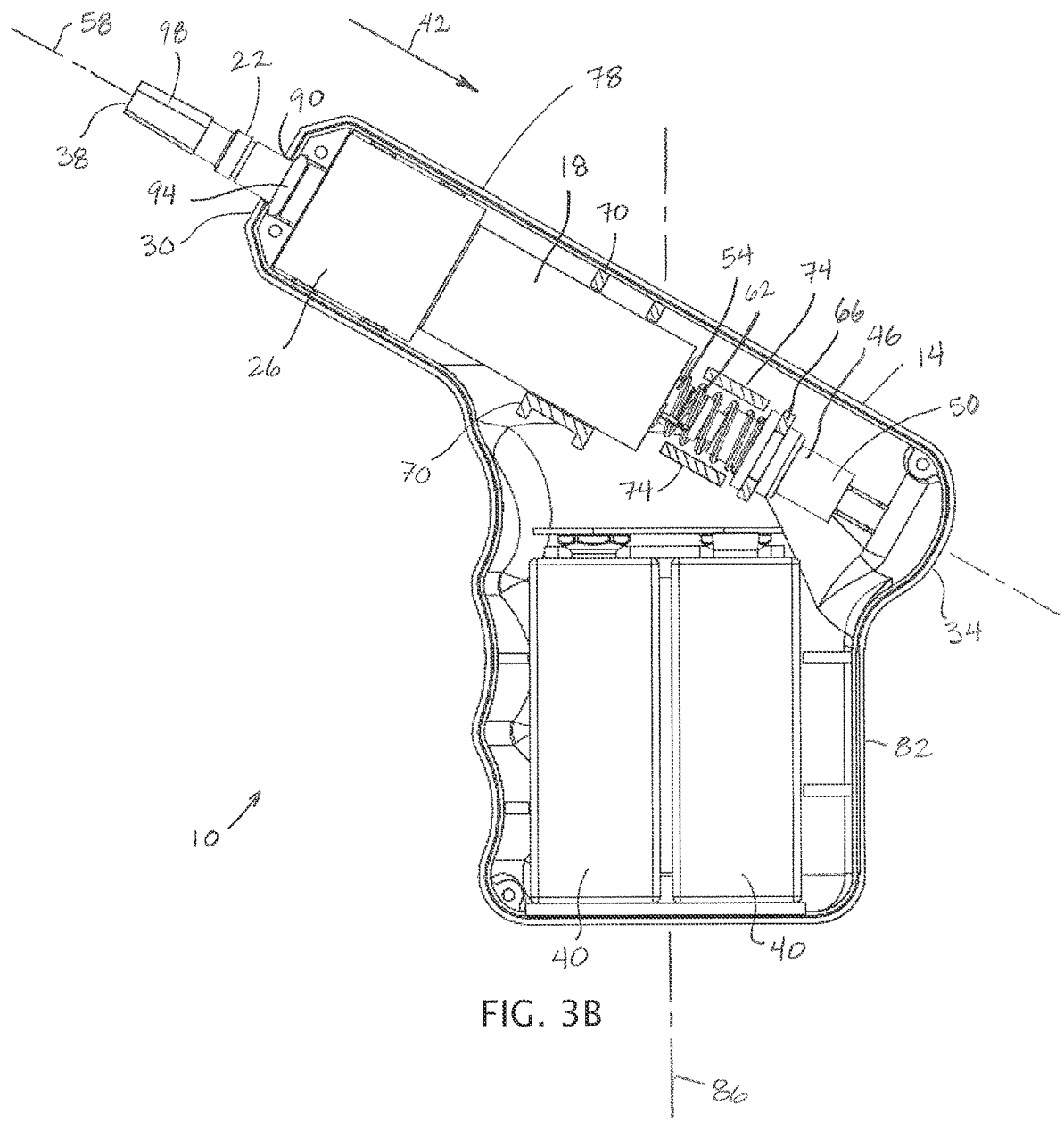

Embodiments of the present powered drivers may be used to insert an IO device incorporating teachings of the present disclosure into a selected target area or target site (e.g., in ten seconds or less).

Vascular system access may be essential for treatment of many serious diseases, chronic conditions, and acute emergency situations. Yet, many patients experience extreme difficulty obtaining effective treatment because of an inability to obtain or maintain intravenous (IV) access. An intraosseous (IO) space provides a direct conduit to a patent's vascular system and systemic circulation. Therefore, IO access is generally an effective route to administer a wide variety of drugs, other medications, and/or IV fluids. Rapid IO access or emergency vascular access (EVA) offers great promise for almost any serious emergency that requires vascular access to administer life-saving drugs, other medications, and/or fluids when traditional IV access is difficult or impossible.

Bone marrow typically includes blood, blood forming cells, and connective tissue disposed in an intraosseous space or cavity surrounded by compact bone. Long bones such as the tibia typically have an elongated central cavity filled with yellow bone marrow and adipose or connective tissue. Such cavities may also be referred to as a "medullary cavity," "bone marrow cavity," and/or "intraosseous space."

Compact bone disposed near an anterior or dorsal surface may be referred to as "anterior compact bone" or "anterior bone cortex." Compact bone disposed farther from the dorsal or anterior surface may be referred to as "posterior compact bone" or "posterior bone cortex."

Examples of insertion sites for an IO device to establish access with a patient's vascular system include the upper tibia proximate a patient's knee, the humeral head proximate a patient's shoulder, and the patient's sternum. Availability of multiple intraosseous insertion sites and associated target areas in adjacent bone marrow have proven to be particularly important in applications such as emergency treatment of battlefield casualties or other mass casualty situations. Teachings of the present disclosure may be used to obtain intraosseous access at a wide variety of insertion sites and target areas.

IO access may be used as a "bridge" for temporary fluid and/or drug therapy during emergency conditions until conventional IV sites can be found and used. Conventional IV sites often become available because fluids and/or medication provided via IO access may stabilize a patient and expand veins and other portions of a patient's vascular system. IO devices and associated procedures incorporating teachings of the present disclosure may become standard care for administering medications and fluids in situations when IV access is difficult or otherwise impossible.

Intraosseous access may be used as a "routine" procedure with chronic conditions which substantially reduce or eliminate availability of conventional IV sites. Examples of such chronic conditions may include, but are not limited to, dialysis patients, patients in intensive care units, and/or epilepsy patients. Intraosseous devices and associated apparatuses incorporating teachings of the present disclosure may be quickly and safely used to provide IO access to a patient's vascular system in difficult cases, such as status epilepticus, to give medical personnel an opportunity to administer crucial medications and/or fluids. Further examples of such acute and chronic conditions are listed near the end of this written description.

Apparatuses and methods incorporating teachings of the present disclosure may include using a first IO needle set having (e.g., a fifteen (15) gauge) cannula with a length of approximately fifteen (15) millimeters to establish vascular access for patients weighing between approximately three (3) kilograms and thirty nine (39) kilograms. A second IO needle set having a (e.g., a fifteen (15) gauge) cannula with an approximate length of twenty-five (25) millimeters may be used to establish vascular access for patients weighing forty (40) kilograms and greater. In other embodiments, a single size of IO needle set having a (e.g., a fifteen (15) gauge) cannula with an approximate length of twenty-five (25) millimeters may be used to establish vascular access for patients weighing three (3) kilograms and greater.

The term "driver" may be used in this application to include any type of powered driver satisfactory for inserting an intraosseous (TO) device such as a penetrator assembly, a catheter, an IO needle, and/or an IO needle set into a selected portion of a patient's vascular system. Various techniques may be satisfactorily used to releasably engage or attach an IO device with a driver incorporating teachings of the present disclosure. A wide variety of connectors and associated connector receptacles, fittings, and/or other types of connections with various dimensions and configurations may be satisfactorily used to releasably engage an IO device with a driver. A battery powered driver incorporating teachings of the present disclosure may be used to insert an intraosseous device into a selected target area in ten (10) seconds or less. The reduced size and weight of drivers incorporating teachings of the present disclosure may accommodate use in emergency medical vehicles, in emergency crash carts at medical facilities and/or in carrying in backpacks of military personnel deployed for extended periods of time in remote locations.

The term "fluid" may be used in this application to include liquids such as, but not limited to, blood, water, saline solutions, IV solutions, plasma, any mixture of liquids, particulate matter, dissolved medication, and/or drugs associated with biopsy and/or aspiration of bone marrow, and/or communication of fluids with bone marrow or other target sites. The term "fluid" may also be used in this patent application to include any body fluids and/or liquids containing particulate matter such as bone marrow and/or cells which may be withdrawn from a target area.

The term "insertion site" may be used in this application to describe a location on a bone at which an intraosseous device may be inserted or drilled into the bone and associated bone marrow. Insertion sites are generally covered by skin and soft tissue. The term "target area" refers to any location on or within biological material, such as the biological material of a human being.

The term "intraosseous (TO) device" may be used in this application to include, but is not limited to, any hollow needle, hollow drill bit, penetrator assembly, bone penetrator, catheter, cannula, trocar, stylet, inner penetrator, outer penetrator, IO needle, biopsy needle, aspiration needle, IO needle set, biopsy needle set, and/or aspiration needle set operable to access or provide access to an intraosseous space or interior portions of a bone. Such IO devices may be formed, at least in part, from metal alloys such as 304 stainless steel and/or other biocompatible materials associated with needles and similar medical devices.

For some applications an IO needle or IO needle set may include a connector with a trocar or stylet extending from a first end of the connector. A second end of the connector may be operable to be releasably engaged with a powered driver incorporating teachings of the present disclosure. An IO needle or IO needle set may also include a hub with a hollow cannula or catheter extending from a first end of the hub. A second end of the hub may include an opening sized to allow inserting the trocar through the opening and the attached hollow cannula. The second end of the hub may be operable to be releasably engaged with the first end of the connector. As previously noted, the second end of the connector may be releasably engaged with a powered driver. A wide variety of connectors and hubs may be used with an IO device incorporating teachings of the present disclosure. The present disclosure is not limited to connector 180 or hub 200 as shown in FIGS. 4A and 4B.

Figure 4A:
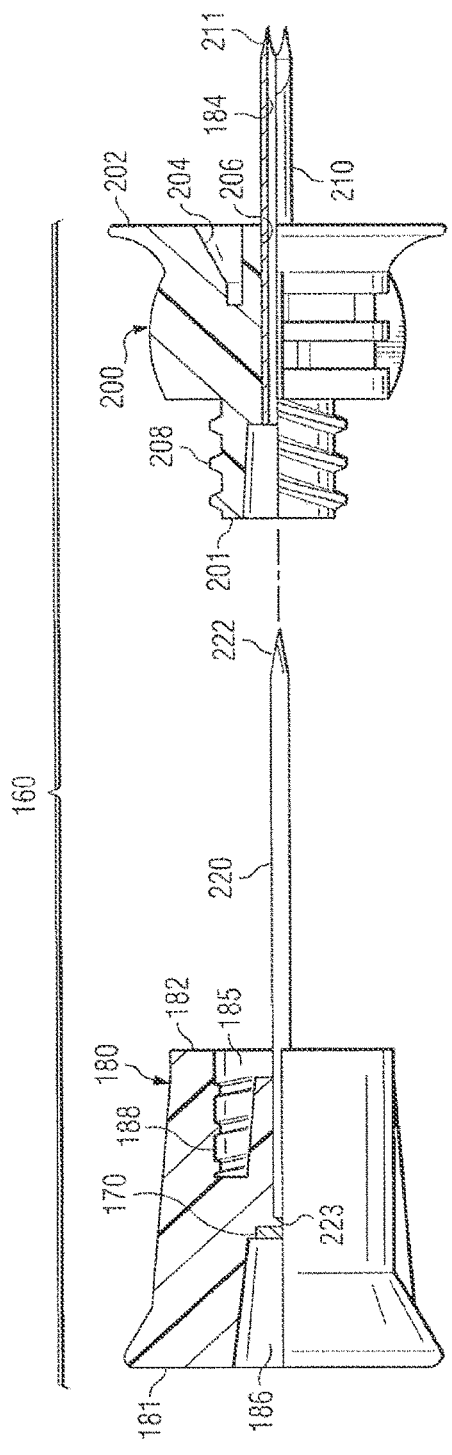
FIG. 4A depicts an exploded and partially cutaway side view of one example of an intraosseous needle set or penetrator assembly which may be inserted into a patient's bone and, thus, into a patient's vascular system using one of the present drivers and may be included in certain ones of the present kits.
Figure 4B:
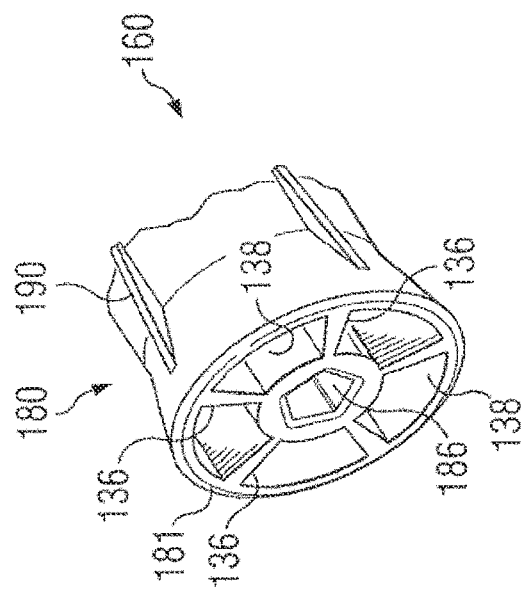
FIG. 4B depicts a partial perspective view of a connector receptacle of the IO needle set of FIG. 4A that may be releasably engaged with embodiments of the present powered drivers.

The IO device shown in FIGS. 4A and 4B is a prior art device, and the description of it is provided to give the reader context for the types of devices and components that can be used consistently with embodiments of the present drivers and kits.

Referring now to the drawings, and more particularly to FIGS. 1-3B, shown therein and designated by the reference numeral 10 is one embodiment of the present apparatuses or powered drivers. Powered driver 10 may be satisfactorily used to insert an intraosseous device at a desired insertion site adjacent to a bone and associated bone marrow. Powered driver 10 may include one or more of the present features. One or more additional and/or alternative ones of the present features may also be included in or with powered driver 10a of FIGS. 5-8.

In the embodiment shown, powered driver 10 includes a housing 14, a motor 18, a driveshaft 22, and a gearbox 26. Housing 14 has a distal end 30 and a proximal end 34, and motor 18 is disposed within the housing with driveshaft 22 extending outwardly from distal end 30 of the housing in a direction away from proximal end 34 such that a distal end 38 of the driveshaft is spaced apart from distal end 30 of the housing. In the embodiment shown, gearbox 26 is coupled to motor 18 and to driveshaft 22 such that activation of the motor will cause rotation of the driveshaft (suitable gearboxes described in more detail below). In this embodiment, driver 10 also comprises a battery (e.g., two batteries 40, as shown) configured to power motor 18 (e.g., through electrical communication between batteries 40 and motor 18, for example, through wiring, circuitry, and/or the like). In the embodiment shown, batteries 40 comprise two 9-volt batteries which may be commercially available from a variety of suppliers and retail outlets. Other embodiments can include any suitable battery and/or combination of batteries that permit the function(s) described in this disclosure.

In the depicted embodiment, driver 10 does not include a "trigger" configured to be squeezed or otherwise depressed with a user's finger during use to activate the motor. Instead, in this embodiment, gearbox 26 is slidably disposed in housing 14 and configured such that, upon application of a threshold force (e.g., a force at least large enough to move the driveshaft) on driveshaft 22 in direction 42 (toward proximal end 34 of the housing), the driveshaft and gearbox will slide toward the proximal end of the housing and thereby close an electrical circuit between the motor and the battery (and thus active the motor to rotate the driveshaft). For example, in the embodiment shown, driver 10 further comprises a switch 46 (e.g., having a body 50 and a piston 54 axially movable relative to the body, as shown) that is coupled to the battery and the motor (e.g., via wires or other conductors), where the switch is disposed between proximal end 34 of the housing and at least a portion of gearbox 26. In this embodiment, switch 46 is configured to close the circuit (e.g., between the battery and the motor upon application of the threshold force on the driveshaft). In this embodiment, motor 18 and gearbox 26 are coupled in fixed axial relation to each other and are together slidable within the housing (e.g., along axis 58). In this embodiment, switch 46 is disposed between motor 18 and proximal end 34 of the housing.

In some embodiments, gearbox 26 (and driveshaft 22) is biased in the direction of distal end 30 (e.g., by a spring 62 disposed between the gearbox and the distal end of the housing) such that in the absence of the threshold force on the driveshaft, the circuit remains open and the motor is not active. For example, in this embodiment, motor 18 and gearbox 26 are together biased in the direction of distal end 30 of the housing by a spring 62 disposed between body 50 of the switch (e.g., and/or one or more tabs or other portions 66 of housing 14 to which the body of the switch is mounted or otherwise supported, such as, for example, against axial movement) and motor 18. In this embodiment, housing 14 includes one or more internal tabs or portions 70 supporting motor 18 (e.g., against lateral displacement relative to axis 58) and permitting the motor to slide axially along axis 58 (e.g., configured to support motor 18 in coaxial alignment with axis 58). In the embodiment shown, housing 14 also includes one or more internal tabs or portions 74 configured to limit the depth of slidable movement of motor 18 (and gearbox 26 and driveshaft 22) in direction 42. In this embodiment, tabs 74 are disposed on opposite sides of spring 62 and extend within a cross-sectional perimeter of a proximal end of motor 18 such that tabs 74 physically limit movement of motor 18 in direction 42. In other embodiments, housing 14 (including tabs or portions 70 and/or 74) can be provided in any structure or configuration that permits the operation describes in this disclosure (e.g., such that axial displacement of motor 18, gearbox 26, and/or driveshaft 22 is limitably permitted and lateral displacement of motor 18, gearbox 26, and/or driveshaft 22 is substantially restricted).

Spring 62 may be configured with a spring constant of between 1 and 6 pounds of force per inch (lbf/in). In various embodiments, spring 62 may be configured differently for different applications. For example, in embodiments of the present drivers that are configured for pediatric use, the spring may be configured with a spring constant of between 1 and 4 lbf/in (e.g., 2-3 lbf/in); in embodiments of the present drivers that are configured for adult tibia and/or humerous insertion, the spring may be configured with a spring constant of between 2 and 6 lbf/in (e.g., 3-5 lbf/in); and, in embodiments of the present drivers that are configured for adult sternal insertions, the spring may be configured with a spring constant of between 1 and 4 lbf/in (e.g., 2-3 lbf/in).

Motors and gear assemblies satisfactory for use with a powered driver incorporating teachings of the present disclosure may be obtained from various vendors. Such motor and gear assemblies are typically ordered as "sets" with one end of each motor securely attached to an adjacent end of an associated gear assembly. A driveshaft having various dimensions and/or configurations may extend from the gear assembly opposite from the motor. The gear assemblies may sometimes be referred to as "reduction gears" or "planetary gears." The dimensions and/or configurations of an associated housing may be modified to accommodate an associated motor and gear assembly.

While driver 10 is configured such that motor 18, gearbox 26, and driveshaft 22 are axially slidable together, other embodiments may be configured such that the motor is held in a fixed axial position relative to the housing and the gearbox and the driveshaft slide relative to the motor (e.g., along a stub shaft extending from the motor), or such that the motor and gearbox are held in a fixed axial position relative to the housing and the driveshaft slides relative to the motor and gearbox, to activate the motor and rotate the driveshaft. In some embodiments, the motor is configured to rotate at a satisfactory speed and a satisfactory torque such that the gearbox can be omitted and the motor can directly drive the driveshaft.

In the embodiment shown, housing 14 defines a primary portion 78 extending between distal end 30 and proximal end 34, and a handle portion 82 (e.g., having a central longitudinal axis 86) extending laterally from primary portion 78 at a non-parallel angle 84 (e.g., between thirty degrees (30°) and sixty degrees (60°), and in some embodiments, up to or greater than ninety degrees)(90°) relative to axis 58 of the primary portion. In this embodiment, housing 14 can be described has having the general configuration of a small pistol (e.g., housing 14 resembles a pistol-grip). Handle portion 82 may be described as an elongated, hollow container sized to receive batteries 40, as shown. Housing 14 may be formed from relatively strong, heavy duty polymeric material. For some applications housing 14 may be formed in two halves which are joined together to form a fluid tight seal with certain components of driver 10 disposed in the housing, as shown. In some embodiments, batteries 40 are not removable from housing 14. For example, two halves of the housing may be glued or otherwise coupled (e.g., welded) together such that the housing generally cannot be reopened (e.g., to replace batteries) without damaging the housing. In other embodiments, batteries 40 may be removable for replacement and/or recharging.

In the embodiment shown, distal end 30 of housing 14 includes an opening 90 with portions of driveshaft 22 extending therethrough. In the embodiments shown driver 10 further includes an O-ring (e.g., a resilient polymeric or rubber O-ring) 94 disposed around driveshaft 22 and between gearbox 26 and distal end 30 of the housing to seal opening 90. In some embodiments, at least a portion (e.g., distal end 38) of driveshaft 22 has an equilateral polygonal cross-sectional shape. For example, in the embodiment shown, a portion of the driveshaft terminating in distal end 38 has a pentagonal cross-sectional shape defined by five surfaces 98. In some embodiments, such as the one shown, surfaces 98 may be tapered and/or disposed at an angle relative to axis 58 (e.g., an angle of three degrees)(3°±two degrees (2°) relative to axis 58). In some embodiments, a magnet can be disposed on and/or in distal end 38 of the driveshaft (e.g., or distal end 38 may otherwise be magnetic). Fittings and/or connectors with various dimensions and/or configurations other than the depicted configuration of distal end 38 of the driveshaft may also be satisfactorily used with a powered driver incorporating teachings of the present disclosure (e.g., in the shown embodiment, distal end 38 of driveshaft 22 is configured to releasably secure IO needle set 160, however, in other embodiments, driveshaft 22 can be configured to releasably secure other IO needle sets and comprise any associated structure).

In the embodiment shown, driveshaft 22 includes an annular groove 102 configured to receive O-ring 94 when driveshaft 22 is pressed fully in direction 42, such that O-ring 94 will contract into groove 102 and prevent driveshaft 22 from returning to its extended position. This is but one example of a way in which driver 10 can be configured as a single-use driver (e.g., to permit the use of inexpensive batteries while preventing re-use to maintain efficacy and patient safety, such as, for example, where the batteries provide sufficient power to insert a single IO device but may not provide sufficient power to insert a second IO device). In other embodiments, switch 46 may be configured as a single-use switch that prevents a second activation, such as, for example, with a fuse that terminates the functionality of the switch after a single use, or a simple timer circuit that terminates the functionality of the switch after a prescribe period of time (e.g., 10 seconds) that is sufficient to insert a single IO device but not sufficient to couple a second IO device to driveshaft 22 and attempt to insert the second IO device. In other embodiments, spring 62 may comprise a collapsible member and/or otherwise be configured to irreversibly yield after compression. In yet other embodiments, similar single-use structure can be provided (e.g., alone or in addition to the above) through collapsible internal support members (e.g., collapsible internal tabs or protrusions 66, 70, and/or 74). In further embodiments, the driver is configured to have sufficient power to insert and/or re-insert up to but not more than a threshold number (e.g., 3, 4, 5, or more) of IO devices such that a user can insert, adjust the depth of, and/or re-insert an IO device with a single driver. In other embodiments, driver 10 can be configured to allow removal of batteries 40 by pressing tabs or snaps incorporated into housing 14. These tabs or snap can be located in the handle portion 82, such as one tab or snap on each side of handle portion 82. Pressing the tabs or snaps causes batteries 40 to be released from driver 10b, such as from the bottom or back side of handle portion 82, and can render the driver inoperable for future use.

Intraosseous (IO) devices having corresponding tapered openings or connector receptacles may be releasably engaged with distal end 38 of driveshaft 22. For example, distal end 38 extending may be releasably engaged with a tapered opening (e.g., 186) in a connector (e.g., 180) as shown in FIGS. 4A and 4B, which depict an example of an IO device or penetrator assembly 160 that is usable with driver 10.

Penetrator assembly 160 as shown in FIGS. 4A and 4B may include connector 180, associated hub 200, outer penetrator 210, and inner penetrator 220. Penetrator assembly 160 may include an outer penetrator such as a cannula, a hollow tube or hollow drill bit, and an inner penetrator such as a stylet or trocar. Various types of stylets and/or trocars may be disposed within an outer penetrator. For some applications, outer penetrator or cannula 210 may be described as a generally elongated tube sized to receive inner penetrator or stylet 220 therein. Portions of inner penetrator 220 may be disposed within longitudinal passageway 184 extending through outer penetrator 210. The outside diameter of inner penetrator 220 and the inside diameter of longitudinal passageway 184 may be selected such that inner penetrator 220 may be slidably disposed within outer penetrator 210.

Metallic disc 170 may be disposed within opening 186 for use in releasably attaching connector 180 with a magnet disposed on distal end 38 of driveshaft 22 (e.g., or an otherwise magnetic driveshaft 22). End 223 of inner penetrator 220 may be spaced from metallic disc 170 with insulating or electrically nonconductive material disposed therebetween. In some embodiments, metallic disc 170 may be magnetic and the distal end 38 of driveshaft 22 and/or driveshaft 22 may comprise metallic materials configured to releasably attach to the magnetic metallic disc of connector 180.

Tip 211 of outer penetrator 210 and/or tip 222 of inner penetrator 220 may be operable to penetrate bone and associated bone marrow. The configuration of tips 211 and/or 222 may be selected to penetrate a bone or other body cavities with minimal trauma. First end or tip 222 of inner penetrator 220 may be trapezoid shaped and may include one or more cutting surfaces. In one embodiment, outer penetrator 210 and inner penetrator 220 may be ground together as one unit during an associated manufacturing process. Providing a matching fit allows respective tips 211 and 222 to act as a single drilling unit which facilitates insertion and minimizes damage as portions of penetrator assembly 160 are inserted into a bone and associated bone marrow. Outer penetrator 210 and/or inner penetrator 220 may be formed from stainless steel, titanium, and/or other materials of suitable strength and durability to penetrate bone.

Hub 200 may be used to stabilize penetrator assembly 160 during insertion of an associated penetrator into a patient's skin, soft tissue, and adjacent bone at a selected insertion site. First end 201 of hub 200 may be operable for releasable engagement or attachment with associated connector 180. Second end 202 of hub 200 may have a size and configuration compatible with an associated insertion site for outer penetrator 210. The combination of hub 200 with outer penetrator 210 may sometimes be referred to as a "penetrator set" or "intraosseous needle."

Connector 180 and attached inner penetrator 220 may be releasably engaged with each other by Luer type fittings, threaded connections, and/or other suitable fittings formed on first end 201 of hub 200. Outer penetrator 210 extends from second end 202 of hub 200.

For some applications connector 180 may be described as a generally cylindrical tube defined in part by first end 181 and second end 182. The exterior of connector 180 may include an enlarged tapered portion adjacent to end 181. A plurality of longitudinal ridges 190 may be formed on the exterior of connector 180 to allow an operator to grasp associated penetrator assembly 160 during attachment with a driveshaft. Longitudinal ridges 190 also allow connector 180 to be grasped for disengagement from hub 200 when outer penetrator 210 has been inserted into a bone and associated bone marrow.

Second end 182 of connector 180 may include opening 185 sized to receive first end 201 of hub 200 therein. Threads 188 may be formed in opening 185 adjacent to second end 182 of connector 180. Threads 188 may be used in releasably attaching connector 180 with threaded fitting 208 adjacent to first end 201 of hub 200.

First end 201 of hub 200 may include a threaded connector 208 and/or other suitable fittings formed on the exterior thereof. First end 201 may have a generally cylindrical pin-type configuration compatible with releasably engaging second end or box end 182 of connector 180.

For some applications end 202 of hub 200 may have the general configuration of a flange. Angular slot or groove 204 sized to receive one end of protective cover or needle cap 234 may be formed in end 202. Slot or groove 204 may be used to releasable engage needle cover 234 (shown in FIG. 5) with penetrator assembly 160.

For some applications a penetrator assembly may include only a single, hollow penetrator. For other applications a penetrator assembly may include an outer penetrator such as a cannula, a hollow needle or hollow drill bit, and an inner penetrator such as a stylet, trocar or other removable device disposed within the outer penetrator. Penetrator 210 is one example of a single, hollow penetrator or cannula.

The size of a penetrator may vary depending upon the intended application for the associated penetrator assembly. Penetrators may be relatively small for pediatric patients, medium size for adults, and large for oversize adults. By way of example, a penetrator may range in length from five (5) mm to thirty (30) mm. The diameter of a penetrator may range from eighteen (18) gauge to ten (10) gauge. The length and diameter of the penetrator used in a particular application may depend on the size of a bone to which the apparatus may be applied. Penetrators may be provided in a wide variety of configurations depending upon intended clinical purposes for insertion of the associated penetrator. For example, there may be one configuration for administering drugs and/or fluids to a patient's bone marrow and an alternative configuration for sampling bone marrow and/or blood from a patient. Other configurations may be appropriate for bone and/or tissue biopsy.

For some applications connector 180 may be described as having a generally cylindrical configuration defined in part by first end 181 and second end 182. Exterior portions of connector 180 may include an enlarged tapered portion adjacent to end 181. A plurality of longitudinal ridges 190 may be formed on the exterior of connector 180 to allow an operator to grasp associated penetrator assembly 160 during attachment with a drive shaft. Longitudinal ridges 190 also allow connector 180 to be grasped for disengagement from hub 200 when outer penetrator 210 has been inserted into a bone and associated bone marrow.

First end 181 of connector of 180 may include opening 186 sized to receive portions driveshaft 22 therein. A plurality of webs 136 may extend radially outward from connector receptacle 186. Webs 136 may cooperate with each other to form a plurality of openings 138 adjacent to first end 181. Opening 186 and openings 138 may cooperate with each other to form portions of a connector receptacle operable to receive respective portions of a connector (not expressly shown) therein.

Figure 5:
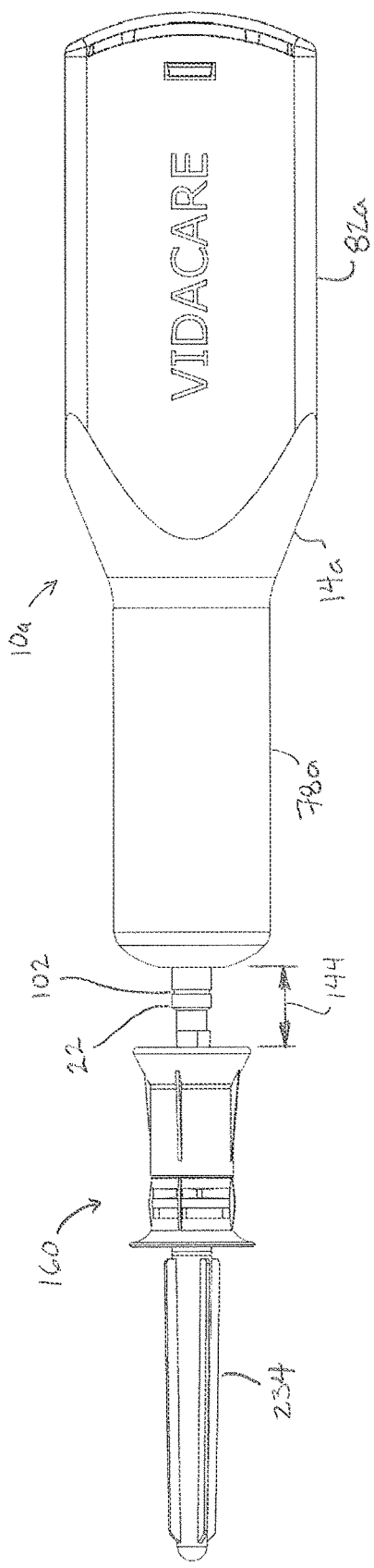
FIGS. 5 and 6 depict side views of a second embodiment of the present drivers with an IO needle set of FIGS. 4A-4B coupled to the driver.
Figure 6:
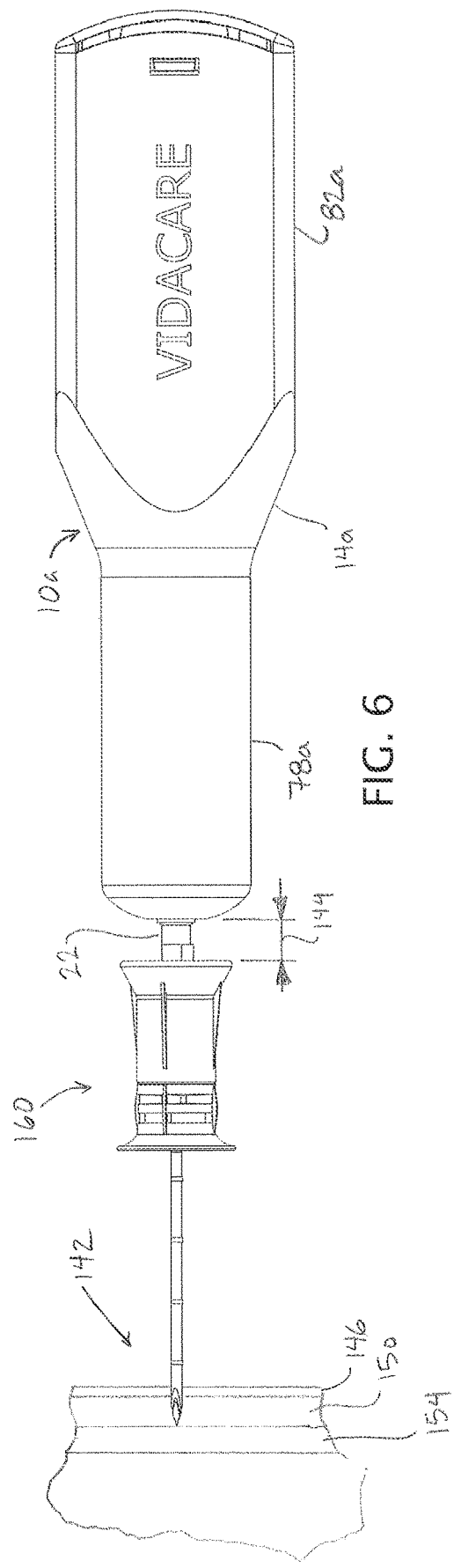
Figure 7:
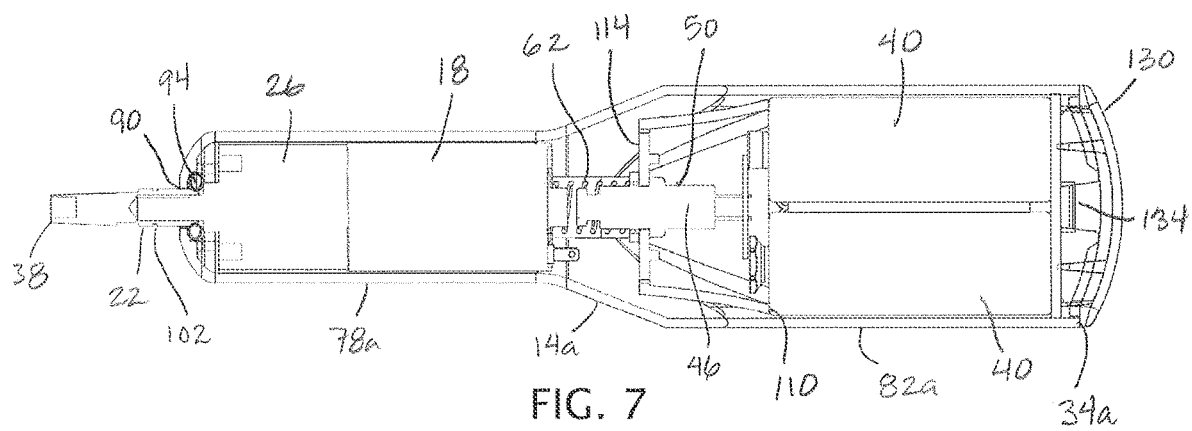
FIG. 7 depicts a side cross-sectional view of the driver of FIGS. 5-6.
Figure 8:
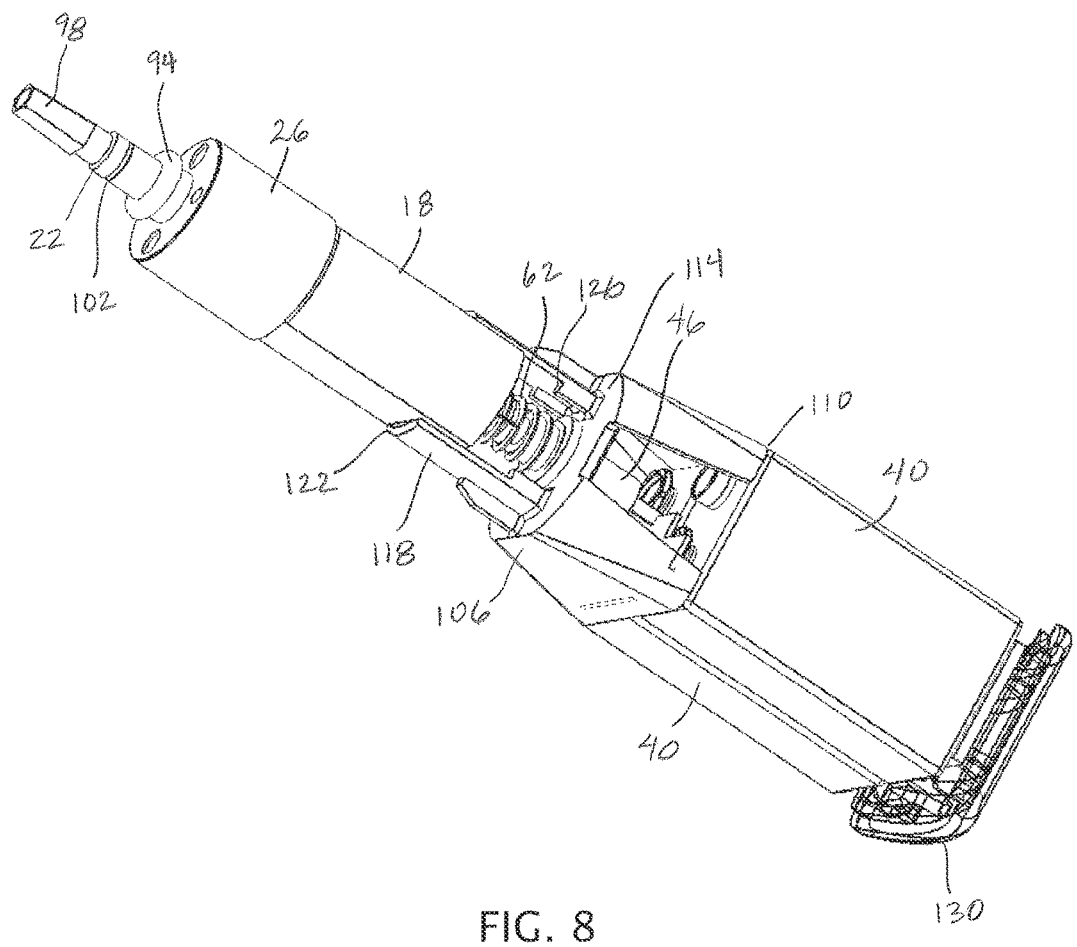
FIG. 8 depicts a cutaway perspective view of the driver of FIGS. 5-6.

Referring now to FIGS. 5-8; FIGS. 5 and 6 depict side views of a second embodiment 10a of the present drivers with an IO needle set 160 (FIGS. 4A-4B) coupled to the driver (e.g., with distal end 38 of driveshaft 22 disposed in a receptacle or recess 186 of the IO needle set); FIG. 7 depicts a side cross-sectional view of driver 10a; and FIG. 8 depicts a cutaway perspective view of driver 10a. Driver 10a is substantially similar to driver 10 with the primary exception that housing 14a of driver 10a is not configured with a pistol-grip design (e.g., does not include a handle portion that is disposed at a non-parallel angle to rotational axis 58 of the driveshaft. As such, similar reference numerals are used to designate components and assemblies that are similar and/or may even be identical (e.g., driveshaft 22 of driver 10 and driveshaft 22 of driver 10a) and dissimilar reference numerals are used to designate components and assemblies that necessarily differ (e.g., driver 10 and driver 10a, housing 14 and housing 14a).

As noted, driver 10a primarily differs from driver 10 in that handle portion 82a of housing 14a is not disposed at a non-parallel angle relative to primary portion 78a; instead, handle portion 82a is parallel to (and, in the depicted embodiment, coaxial with) primary portion 78a. In this embodiment, driver 10a comprises a switch mount 106 having a proximal end 110, a shelf 114 spaced from proximal end 110, and a pair of stepped motor guides 118 extending to a distal end 122 and including steps 126. In the depicted embodiment, shelf 114 is configured to be coupled to body 50 of switch 46, and proximal end 110 is configured to contact batteries 40 to prevent axial movement of the switch body when driver 10a is assembled. In this embodiment, motor guides 118 extend parallel to planar sides of motor 18 and steps 126 limit axial movement of motor 18 relative to housing 14a (e.g., similar to as described above for tabs 74 of driver 10). In this embodiment, housing 14a includes an open proximal end 34a and an end cap 130 is configured enclose the open proximal end (e.g., as shown). In the embodiment shown, end cap 130 includes barbed tabs 134 configured to extend into corresponding openings in housing 14*a* to resist separation of end cap 130 from housing 14*a*. In some embodiments, end cap 130 is additionally or alternatively coupled to housing 14*a* with adhesive, welds, and/or the like such that end cap 130 is not removable from housing 14*a* without damaging end cap 130 and/or housing 14*a*.

In operation, an IO needle set 160 can be coupled to driveshaft 22 (e.g., with needle cover 234 disposed over cannula 210 and trocar 220 and received in annular groove 204, which is then removed prior to positioning the needle set for use). A distal end of the IO needle set can then be disposed at a desired insertion site 142 on a patient and a force applied to the distal end of the IO device via the housing of the driver such that the driveshaft of the driver slides toward proximal end 34 of the housing relative to the housing (as illustrated by the change in dimension 144 between FIGS. 5 and 6) and activates the motor of the driver (e.g., via operation of switch 46) to rotate the driveshaft and IO device. As illustrated, the needle set may puncture skin 146 and soft tissue 150 such that the force may be applied to the IO needle set and driveshaft by a layer of cortical bone 154 responsive to the force applied by a user on the housing in the direction of the insertion site. Alternatively, the threshold force required to move driveshaft 22 toward proximal end 34 may be low enough (e.g., spring 62 may be weak enough), that driveshaft 22 begins to move before the skin is punctured or before all of soft tissue 150 is penetrated. While described with reference to driver 10*a*, the function of driver 10 is substantially similar in that application of a threshold force to housing 14 in the direction of an insertion site will cause motor activation via operation of switch 46, and thus rotation of the driveshaft and IO device.

Embodiments of the present kits can comprise an embodiment of the present drivers (e.g., 10, 10*a*) and an IO device (e.g., 160). Some embodiments of the present kits are sterile.

Figure 9A:
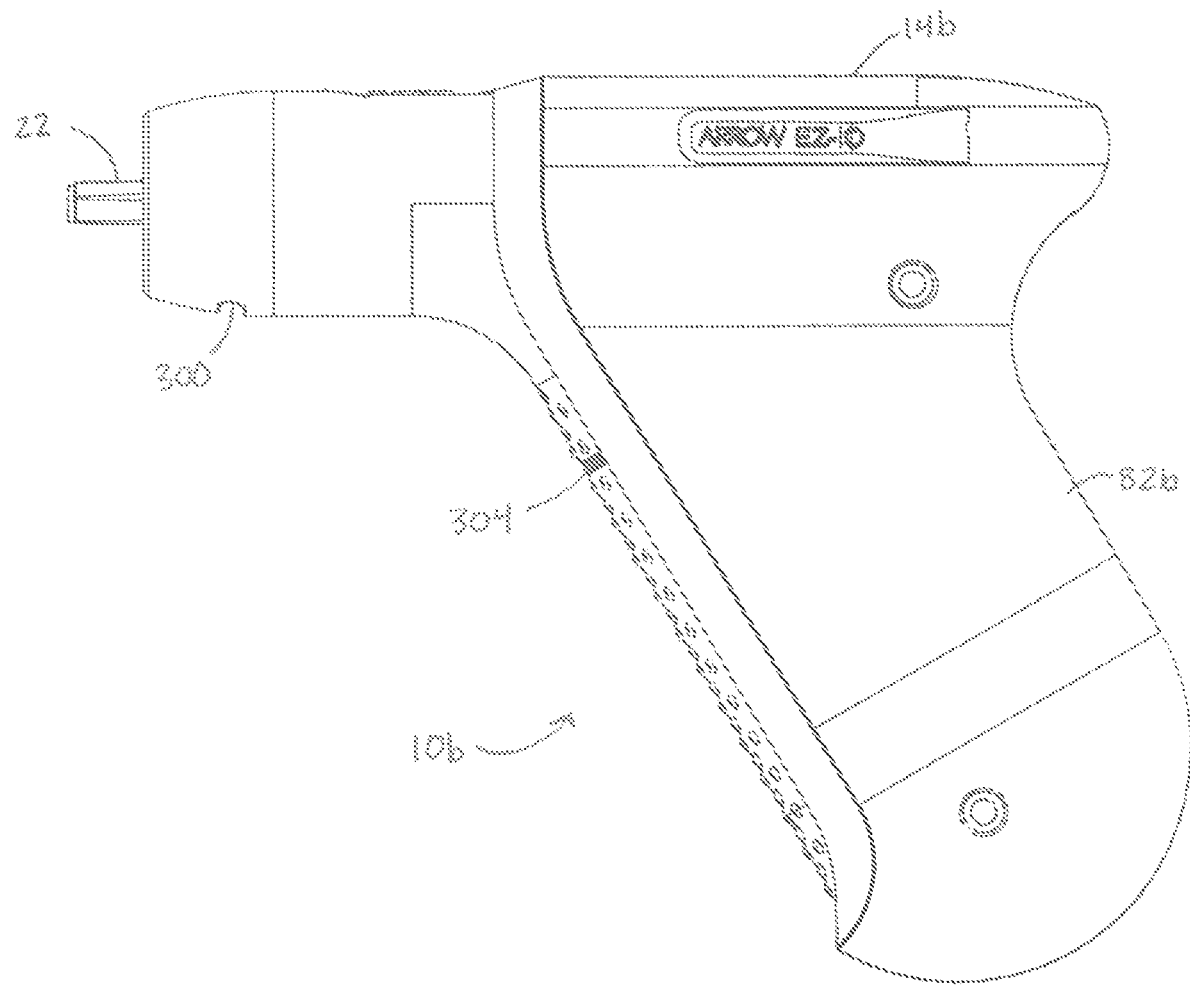
FIGS. 9A-9C depict various views of another embodiment of the present drivers with a more ergonomic handle.
Figure 9B:
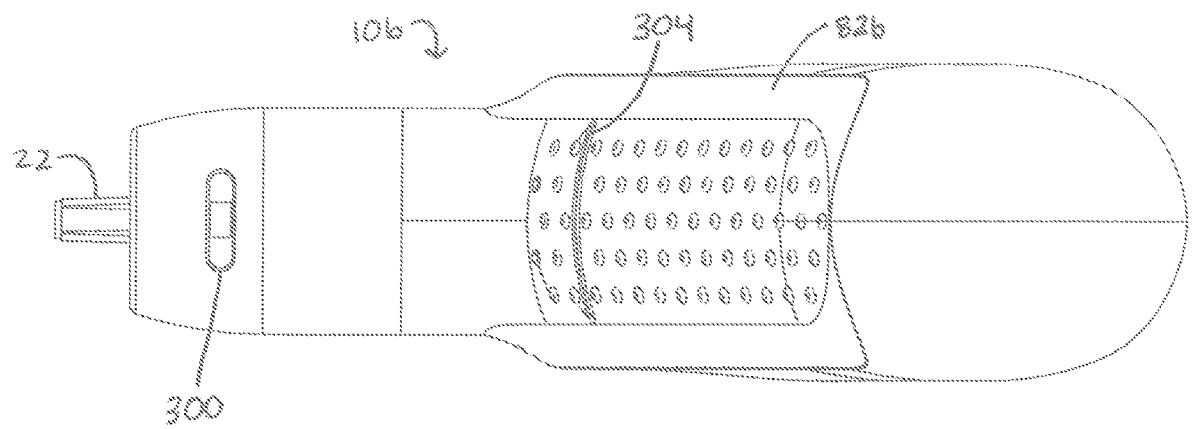
Figure 9C:
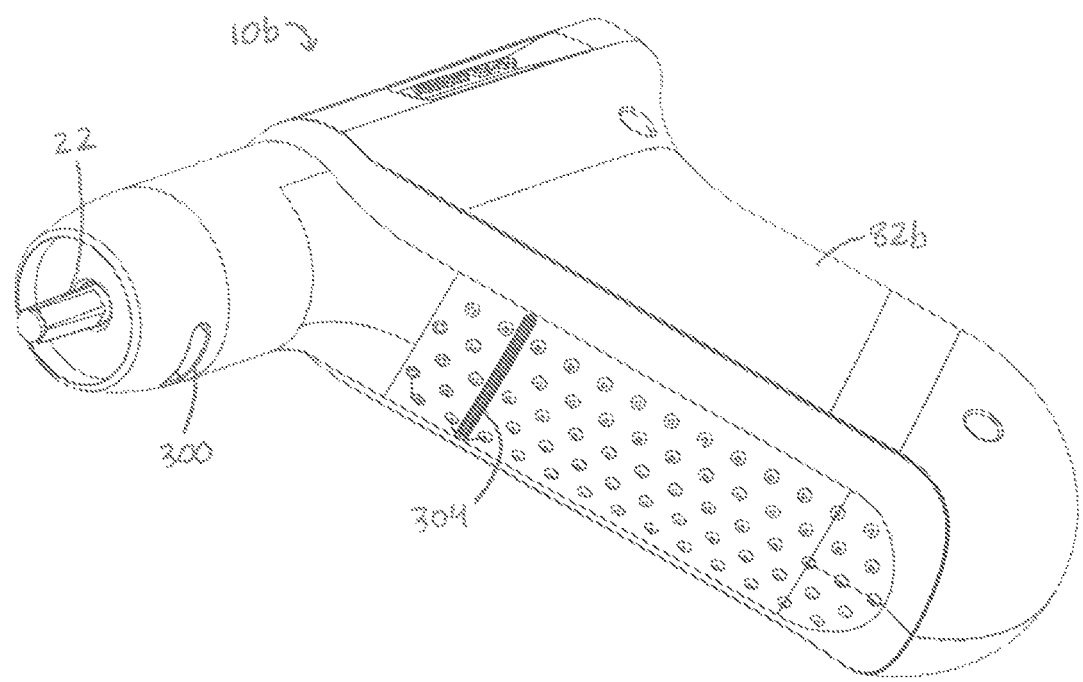

FIGS. 9A-9C depict various views of another embodiment of driver 10*b*. Driver 10*b* is substantially similar in many respects to driver 10, with the primary exceptions that: (1) handle portion 82*b* is shaped for improved ergonomics, (2) housing 14*b* includes slot 300 configured to receive a portion of a mechanical lockout to prevent accidental activation of driver 10*b* for increased safety when handling driver 10*b*, and (3) housing 14*b* includes a slot 304 in handle portion 82*b* configured to receive a portion of an electrical lockout for increased safety when handling driver 10*b*. In this embodiment, slot 300 is sized and positioned to allow a portion of a mechanical lockout to be inserted into housing 14*b* to prevent rearward movement of driveshaft 22 and thereby prevent closing of the electrical circuit that activates driver 10*b*. Similarly, in the depicted embodiment, slot 304 is sized and positioned to allow a portion of an electrical lockout to be inserted into housing 14*b* to prevent the electrical circuit from being closed and thereby energizing driver 10*b* (e.g., to prevent activation of the driver during sterilization, packaging, transportation, or the like).

Figure 10A:
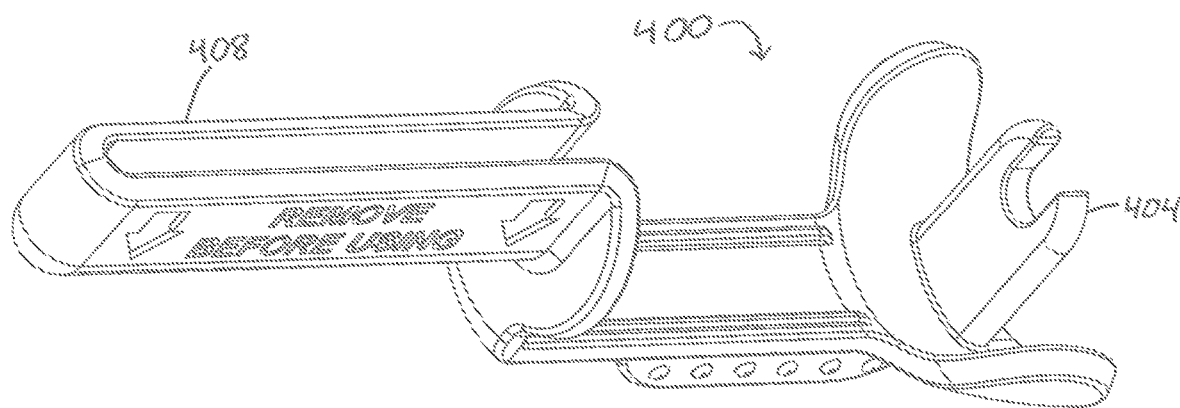
FIG. 10A depicts a perspective view of a mechanical lockout for use with the driver of FIGS. 9A-9C.
Figure 10B:
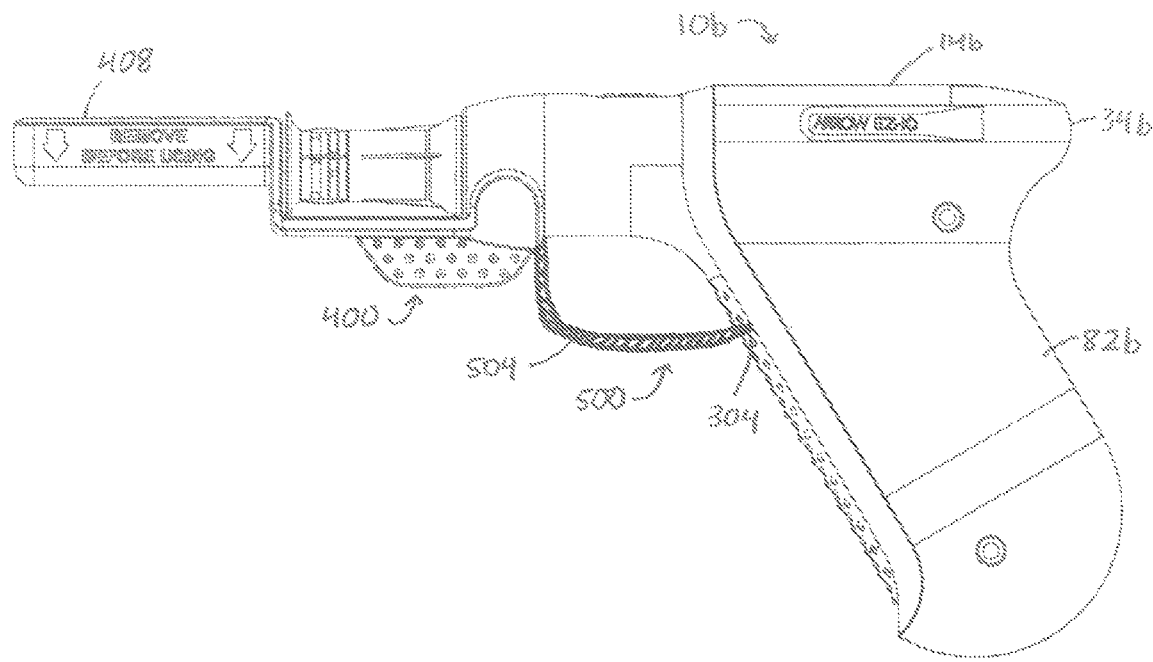
FIGS. 10B and 10C depict side and perspective views, respectively, of the mechanical lockout of FIG. 10A and an electrical lockout in combination with the driver of FIGS. 9A-9C.
Figure 10C:
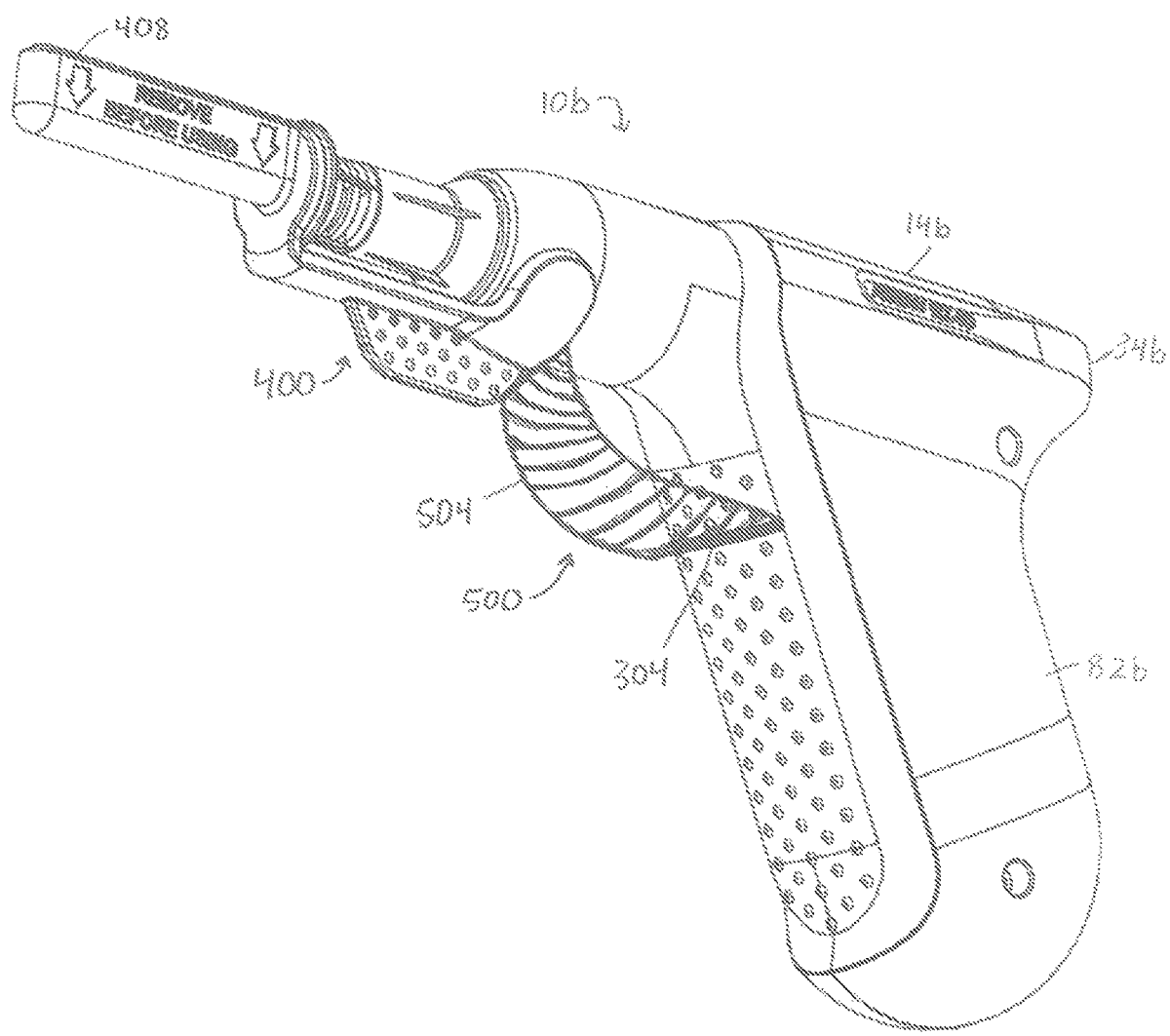

Referring now to FIGS. 10A-10C, FIG. 10A depicts a perspective view of a first embodiment of mechanical lockout 400 for use with driver 10*b* of FIGS. 9A-9C. In this embodiment, mechanical lockout 400 is configured to be coupled to driver 10*b* to prevent accidental activation of driver 10*b* (e.g., for increased safety when handling driver 10*b*, such as during sterilization or transportation). FIGS. 10B and 10C depict side and perspective views, respectively, of mechanical lockout 400 of FIG. 10A, and an embodiment of an electrical lockout 500, in combination with driver 10*b* of FIGS. 9A-9C. As shown, mechanical lockout 400 is removably engaged with driver 10*b* with tab 404 of the mechanical lockout be removably inserted into slot 300 in housing 14*b* proximal to at least a portion of driveshaft 22.

Figure 11:
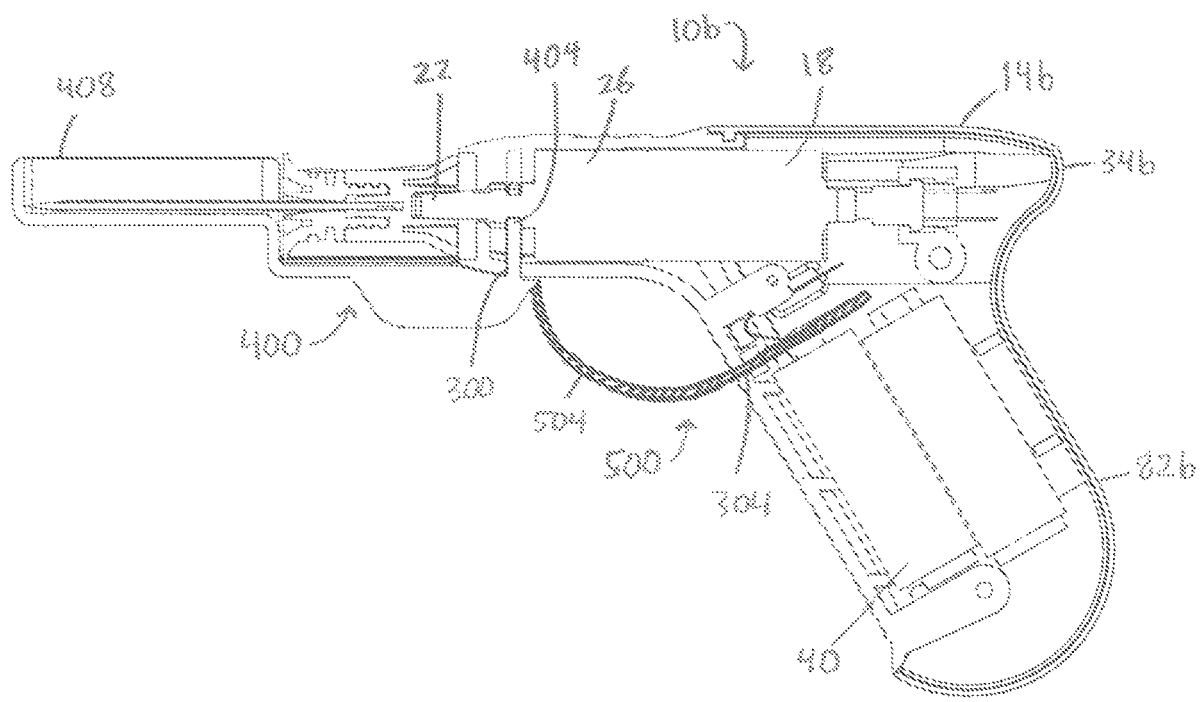
FIG. 11 depicts a cross-sectional view of the lockouts of FIGS. 10B and 10C in combination with the driver of FIGS. 9A-9C.

For example, as illustrated in FIG. 11, tab 404 extends into slot 300 and is shaped to extend around and receive a reduced-diameter part of driveshaft 22 (e.g., in a recess, as shown) to physically impede rearward movement of driveshaft 22 and gearbox 26. In other embodiments, slot 300 could be located in housing 14*b* closer to proximal end 34*b* of housing 14*b* and still physically impede rearward movement to prevent accidental activation. For instance, slot 300 can be located proximal to a portion (e.g., all) of gearbox 26, or a portion (e.g., all) of motor 18. In the embodiment illustrated in FIG. 11, upon application of a threshold force on driveshaft 22 in the direction of proximal end 34*b* of housing 14*b*, mechanical lockout 400 prevents driveshaft 22 and gearbox 26 from sliding toward proximal end 34*b* of housing 14*b*, which prevents driveshaft 22 and gearbox 26 from closing the electrical circuit between motor 18 and battery 40. In this embodiment, mechanical lockout 400 also includes needle cover 408.

FIG. 11 depicts a cross-sectional view of the lockouts of FIGS. 10B and 10C in combination with driver 10*b*. FIG. 11 depicts an embodiment of electrical lockout 500 for increased safety when handling driver 10*b*, such as during sterilization. Electrical lockout 500 comprises flexible strip 504 that is removably inserted into slot 304 in housing 14*b* in handle portion 82*b* between two electrically conductive portions of the electrical circuit to prevent driver 10*b* from energizing during sterilization. In this embodiment, strip 504 can comprise a polymer, such as Mylar, and/or other non-conductive material. Electrical lockout 500 can be used with driver 10*b* in conjunction with any embodiment of the present mechanical lockouts (e.g., mechanical lockout 400 or mechanical lockout 400*a*). As shown, electrical lockout 500 can be coupled to mechanical lockout 400. Coupling can be achieved, for example, by attaching strip 504 to mechanical lockout 400, such as at the proximal end of mechanical lockout 400, so that strip 504 and electrical lockout 500 can be removed in a single pull when removing mechanical lockout 400.

Figure 12A:
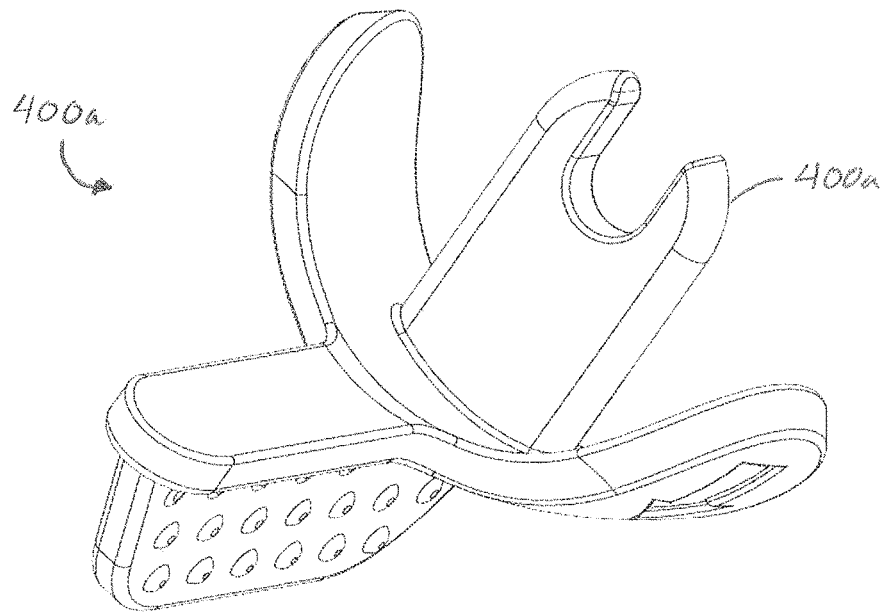
FIG. 12A depicts a perspective view of a second embodiment of a mechanical lockout for use with the driver of FIGS. 9A-9C.
Figure 12B:
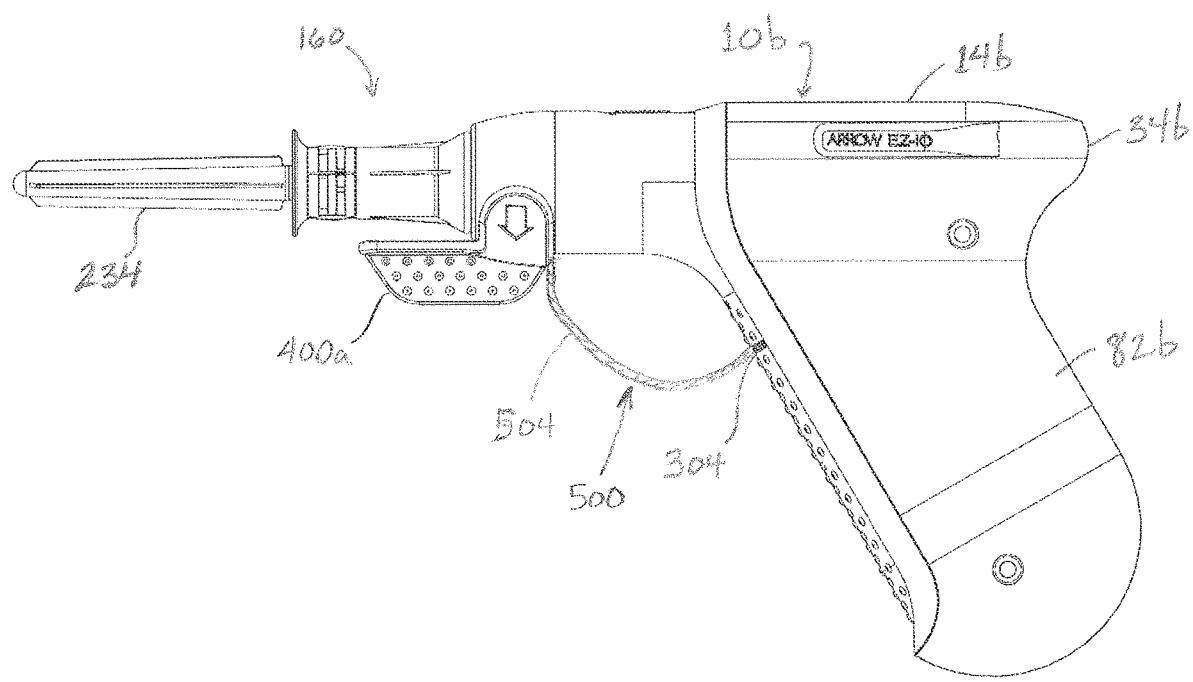
FIG. 12B depicts a side view of the mechanical lockout of FIG. 12A and an electrical lockout in combination with the driver of FIGS. 9A-9C.

FIG. 12A depicts a perspective view of a second embodiment of mechanical lockout 400*a* for use with driver 10*b* to prevent accidental activation of driver 10*b* (e.g., for increased safety when handling driver 10*b*, such as during sterilization, transportation, or when applying a needle set 160 to driver 10*b*). Mechanical lockout 400*a* is similar to mechanical lockout 400, but does not include a needle cover. FIG. 12B depicts a side view of mechanical lockout 400*a* of FIG. 12A and electrical lockout 500 in combination with driver 10*b*. In other embodiments, mechanical lockout 400*a* can also be used with driver 10*b* without an electrical lockout. As depicted in FIG. 12B, mechanical lockout 400*a* is removably engaged with driver 10*b*. Mechanical lockout 400*a* includes tab 404*a*, and similar to FIG. 11, tab 404*a* can be removably inserted into slot 300 in housing 14*b* proximal to at least a portion of driveshaft 22. Similar to FIG. 11, upon application of a threshold force on driveshaft 22 in the direction of proximal end 34*b* of housing 14*b*, mechanical lockout 400*a* prevents driveshaft 22 and gearbox 26 from sliding toward proximal end 34*b* of housing 14*b*, which prevents driveshaft 22 and gearbox 26 from closing the electrical circuit between motor 18 and battery 40.

The above specification and examples provide a complete description of the structure and use of illustrative embodiments. Although certain embodiments have been described above with a certain degree of particularity, or with reference to one or more individual embodiments, those skilled in the art could make numerous alterations to the disclosed embodiments without departing from the scope of this invention. As such, the various illustrative embodiments of the methods and systems are not intended to be limited to the particular forms disclosed. Rather, they include all modifications and alternatives falling within the scope of the claims, and embodiments other than the one shown may include some or all of the features of the depicted embodiment. For example, elements may be omitted or combined as a unitary structure, and/or connections may be substituted. Further, where appropriate, aspects of any of the examples described above may be combined with aspects of any of the other examples described to form further examples having comparable or different properties and/or functions, and addressing the same or different problems. Similarly, it will be understood that the benefits and advantages described above may relate to one embodiment or may relate to several embodiments.

The claims are not intended to include, and should not be interpreted to include, means-plus- or step-plus-function limitations, unless such a limitation is explicitly recited in a given claim using the phrase(s) "means for" or "step for," respectively.

The invention claimed is:

1. A driver operable to insert an intraosseous device into a bone, the driver comprising:
   a housing having a distal end and a proximal end;
   a driveshaft near the distal end of the housing, the drive shaft configured to engage a portion of the intraosseous device;
   a motor disposed in the housing and operable to rotate the driveshaft;
   a power source disposed within the housing and configured to power the motor; and
   a lockout operable to prevent activation of the driver for increased safety when handling the driver;
   wherein the housing includes a slot configured to receive a portion of the lockout, and wherein the lockout is configured to be removably inserted into the slot in the housing to prevent an electrical circuit from being closed thereby preventing activation of the driver.

2. The driver according to claim 1, wherein the lockout comprises a non-conductive material.

3. The driver according to claim 1, wherein the housing defines a primary portion and a handle portion, the primary portion extending between the distal end and the proximal end, and the handle portion extending from the primary portion.

4. The driver according claim 3, wherein the slot is located in the handle portion of the housing.

5. The driver according to claim 4, wherein the intraosseous device comprises an intraosseous needle set.

6. The driver according to claim 5, wherein the intraosseous needle set comprises an inner penetrator and an outer penetrator, the inner penetrator slidably disposed within the outer penetrator.

7. The driver according to claim 5, wherein the driveshaft is configured to releasably secure the intraosseous needle set.

8. The driver according to claim 3, wherein the power source comprises a battery.

9. The driver according to claim 8, wherein the driver is a single-use driver.

10. The driver according to claim 9, wherein the driveshaft includes an annular groove configured to receive an O-ring when the driveshaft moves from a first position to a second position to prevent the driveshaft from returning to the first position.

11. The driver according to claim 9, further comprising a single-use switch configured to prevent a second activation of the driver.

12. The driver according to claim 11, further comprising a fuse operable to terminate functionality of the switch after a single use.

13. The driver according to claim 11, further comprising a timer circuit operable to terminate functionality of the switch after a prescribed period of time.

14. The driver according to claim 9, further comprising a collapsible internal support member configured to prevent a second activation of the driver.

15. The driver according to claim 8, wherein the battery has sufficient power to insert up to but not more than a threshold number of intraosseous devices.

16. The driver according to claim 8, wherein the handle portion of the housing further comprises a tab operable to release the battery from the driver when the tab is pressed.

17. A driver operable to insert an intraosseous device into a bone, the driver comprising:
    a housing having a distal end and a proximal end;
    a driveshaft near the distal end of the housing, the drive shaft configured to engage a portion of the intraosseous device;
    a motor disposed in the housing and operable to rotate the driveshaft;
    a power source disposed within the housing and configured to power the motor; and
    a lockout operable to prevent activation of the driver for increased safety when handling the driver;
    wherein the driveshaft includes an annular groove configured to receive an O-ring when the driveshaft moves from a first position to a second position to prevent the driveshaft from returning to the first position.

18. The driver according to claim 17, wherein the power source comprises a battery.

19. The driver according to claim 17, wherein the housing defines a primary portion and a handle portion, the primary portion extending between the distal end and the proximal end, and the handle portion extending from the primary portion.

20. The driver according to claim 17, wherein the intraosseous device comprises an intraosseous needle set including an inner penetrator slidably disposed within an outer penetrator.

* * * * *